United States Patent [19]

Willis

[11] Patent Number: 5,747,666
[45] Date of Patent: May 5, 1998

[54] POINT-OF-CARE ANALYZER MODULE

[76] Inventor: John P. Willis, 24 Whitney Rd., Shirley, Mass. 01464

[21] Appl. No.: 824,401

[22] Filed: Mar. 26, 1997

Related U.S. Application Data

[60] Provisional application No. 60/014,606 Mar. 29, 1996.

[51] Int. Cl.[6] .................................................. G01C 17/38
[52] U.S. Cl. .......................... 73/1.02; 73/1.01; 324/438; 204/194
[58] Field of Search ........................... 73/1.01, 1.02, 73/1.03, 1.04; 324/438; 204/193, 400, 194, 403

[56] References Cited

U.S. PATENT DOCUMENTS

| | | | |
|---|---|---|---|
| 4,266,941 | 5/1981 | Sullivan | 23/230 B |
| 4,272,245 | 6/1981 | Diamond et al. | 23/230 B |
| 4,301,412 | 11/1981 | Hill et al. | 324/442 |
| 4,301,414 | 11/1981 | Hill et al. | 324/446 |
| 4,336,121 | 6/1982 | Enzer et al. | 204/195 R |
| 4,342,964 | 8/1982 | Diamond et al. | 324/450 |
| 4,397,725 | 8/1983 | Enzer et al. | 204/406 |
| 4,436,610 | 3/1984 | Enzer et al. | 204/400 |
| 4,535,786 | 8/1985 | Kater | 128/760 |
| 4,608,148 | 8/1986 | Frollini, Jr. et al. | 324/438 |
| 4,627,893 | 12/1986 | Cormier et al. | 73/1.02 |
| 4,654,127 | 3/1987 | Baker et al. | 204/1 T |
| 4,734,184 | 3/1988 | Burleigh et al. | 204/409 |
| 4,863,016 | 9/1989 | Grabenkort et al. | 206/210 |
| 5,022,980 | 6/1991 | Tanaka et al. | 73/1.02 |
| 5,080,865 | 1/1992 | Leiner et al. | 422/68.1 |
| 5,089,421 | 2/1992 | Dieffenbach | 436/68 |
| 5,096,669 | 3/1992 | Lauks et al. | 422/61 |
| 5,243,982 | 9/1993 | Mostl et al. | 128/632 |
| 5,284,568 | 2/1994 | Pace et al. | 204/403 |
| 5,325,853 | 7/1994 | Morris et al. | 128/630 |
| 5,330,634 | 7/1994 | Wong et al. | 204/409 |

*Primary Examiner*—George M. Dombroske
*Assistant Examiner*—Max H. Noori
*Attorney, Agent, or Firm*—Lahive & Cockfield LLP

[57] ABSTRACT

A point-of-care analyzer unit characterized by a disposable sensor module, a capability of cooperation with multiple fluid sources for providing multi-point calibration, which sources are detachably connectable with the sensor module, and a waste reservoir integral with the sensor module operable to receive and house multiple sets of complete test sequences comprising multiple calibration fluids sets and an analyte sample.

9 Claims, 4 Drawing Sheets

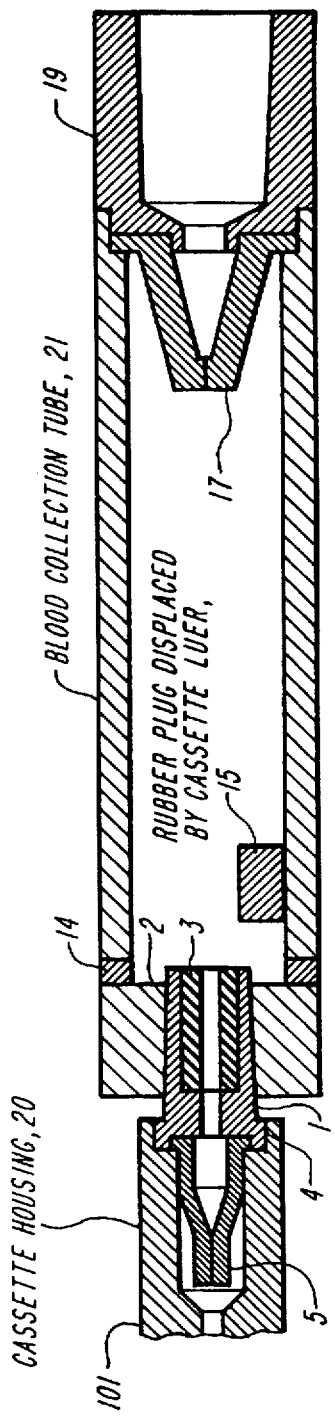
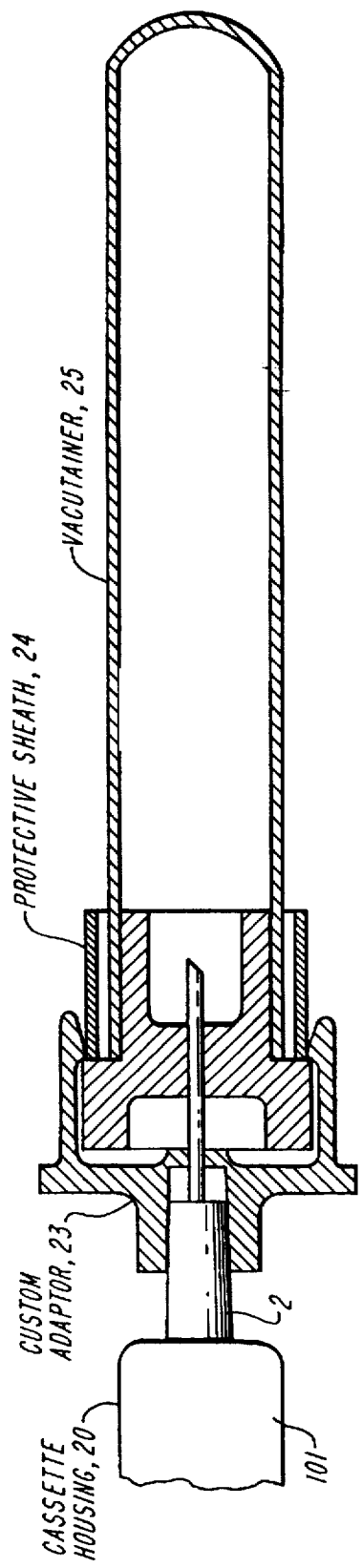

POINT-OF-CARE ANALYZER MODULE

GENERAL BACKGROUND AND SUMMARY OF INVENTION

This invention pertains to an improved, point-of-care analyzer module which is characterized by:

1. A disposable, multi-electrode, multi conditioning sensing, sensor module;
2. A capability of utilizing a plurality of fluid sources to permit multi-point calibration, which sources are detachably connectable with the sensor module; and
3. A waste reservoir integral with the sensor module and operable to receive multiple sets of complete test sequences, with each such sequence being operable to comprise a first calibration, an analyte measurement, and a second calibration.

RELATED APPLICATION

This application claims priority in relation to Applicant's U.S. Provisional Pat. Application Ser. No. 60/014,606, filed Mar. 29, 1996, entitled "Improved Point-Of-Care Analyzer", and identifying John P. Willis as inventor.

GENERAL TECHNOLOGY BACKGROUND

Ever since the advent of hand-held blood glucose monitors in the mid-1980's, clinicians have expected point-of-care (POC) testing to become the wave of the future. However, it has only been in the last few years that technology and the regulatory environment have advanced sufficiently to make POC testing a reality. The increased ability to handle micro samples (<500 uL), ease of use, speed, automation and health care reform have fostered market development.

Moving patient testing to the point-of-care reduces turn-around time. Market segment tailored and clinically useful panels of electrolytes, metabolites and blood gases incorporated in a portable, fast, easy to use and inexpensive format will give health care workers more flexibility in treatment. This will result in a dramatic reduction in the therapeutic turn-around time (TTAT) which is defined as the time from the need for results to the time when a physician can initiate a change in patient treatment. In many instances, the TTAT may be less than 5 minutes; whereas, the current laboratory turn-around time is on the order of 20–30 minutes. Faster turn-around-time can prevent a patient with multisystem complications in an intensive care unit (ICU) from deteriorating, if treatment can begin immediately.

Because POC testing yields almost instantaneous results, little clinical change occurs between the time of specimen collection and test reporting thus, little pre-analytical variation occurs with short turn-around time, thereby eliminating degradation of clinical information, and permitting therapeutic decision making based on currently relevant information.

When a physician is examining an acutely ill patient for which the diagnosis is uncertain, instant results for biochemical tests complement the clinical history and physical examination, and also provide an immediate assessment of patient status for diagnostic purposes or as a guide to the initiation of therapy.

Bedside POC testing also has indirect but equally important advantages such as a reduced possibility for:

specimen loss, inaccurate labeling causing specimen cancellation and reorder, inappropriate specimen transport methods and prolonged time before transport, errors in transmission, transcription and distribution, as well as frequent frustration by nurses and medical staff with delayed results.

In the near future, electroanalytical biosensor systems will have a significant impact on clinical chemistry, particularly as device applications move from the central laboratory to the hospital bedside. Biosensors offer real potential for the decentralization of hospital testing. Stand-alone, biosensor-based instruments are capable of extending real-time, on-line biochemical testing to the patient's bedside, eliminating time-consuming and costly specimen collection, handling and reporting.

An equally large, but more distributed market is physician's office laboratories (POL's) which may be considered to be a sub-species of POC. In the mid-eighties, this market was contemplated as the next frontier in clinical laboratory testing. This market did not materialize due to fears that over-regulation would make POL's unprofitable. These fears were well founded, especially due to federal and state regulations. In the current atmosphere of deregulation, restrictions on POL's may soon be relaxed.

In response to the factors noted above, the present invention is provided and may reside in a small, portable, analytical instrument, weighing on the order 5 lbs, which utilizes a limited reusable, multi-parameter sensor array capable of interfacing with different types of blood-sampling devices including vacutainers, syringes, capillary tubes, arterial lines or central venous catheters. The instrument may be operable to cause the displaying and printing of results. The unit may include two-way wireless data communication to hospital computer networks. This will enable retrieval of previous test results, real time trend analysis and immediate access to reports. In addition, a serial interface and modem may be made available. Patient and operator ID could be entered via a wand-style bar code reader or key pad. A small integrated modem and 500 Mb hard drive could be built into each instrument. All patient and quality control data could thus be accessed at any time. Previous test results, patient trend lines and reports could be easily generated.

Two-point calibration and analysis are uniquely under instrument control in this invention. A feature not found in competitive products is the unique manner in which the instrument performs calibration. Instead of pumps, actuators, air bladders, calibration fluid reservoirs and gels within the disposable, the tenometered calibrators of this invention may be packaged in small (100 mL), pressurized aluminum cylinders which automatically interface to the sensor array when it is inserted into the instrument. The cylinders may contain enough fluid for 500 tests. The calibrators could be sold as a tandem unit which could be removed and replaced in less than a minute. A two point calibration will be performed with each test. Fluid will flow under pressure from within the calibration cylinder.

The removable test element or module consists of a reusable, biosensor array assembled from injection-molded plastic parts. The device is intended to be used for multiple tests and is designed for organ or hospital unit specific combinations of tests and has space for up to twenty-five analytes, for example. It is small, compact and easily fits into the palm of the hand.

To perform a test, the user removes the sensor array from its package and places it in the instrument. The instrument reads lot specific information, warms the device to 37° C. and performs a calibration. This may require about 90 sec.

A "ready" prompt may be displayed and the user instructed to "insert sample".

The user attaches the whole blood sampling device to the sensor array and the analyzer automatically initiates the test sequence. Results may be displayed and printed within about two minutes. Since the analytical element is a closed system, once the blood enters it can not leave. The closed system and unique sampling interface minimize sample handling and transfer. The overflow reservoir within the test element contains a bacteriocide and may have enough overflow volume for 25 tests, for example. Since the test element is reusable, as soon as the first test is complete, another test can be run immediately.

There is no need to remove the sensor array and replace it with a new one each time a test is run. Each sensor array is programmed to perform 25 tests, for example. A message will prompt the user to replace the array after these tests. In addition, when tests are performed, the blood sample is measured on the same device, so there is added assurance that the device is performing properly. This is not the case with a single use device.

Representative tests may embrace measurements of the following parameters:

| Parameter | Measurement Range | SI Units |
|---|---|---|
| pO2 | 1–20 | KPa |
| pCO2 | 1–15 | KPa |
| pH | 6.80–7.80 | |
| Sodium | 100–200 | mmol/L |
| Potassium | 1–10 | mmol/L |
| Chloride | 50–170 | mmol/L |
| Ionized Calcium | 0.5–2.0 | mmol/L |
| Glucose | 2–50 | mmol/L |
| Lactate | 0.1–20 | mmol/L |
| Hematocrit | 0–65 | % |

Calculated parameters may include:
Bicarbonate
Total CO2
Base Excess
Oxygen Saturation
Hemoglobin
Osmolality
Anion Gap

GENERAL STATE OF THE ART

The prior art indicates that it is known to provide disposable, point-of-care analytical units containing disposable electrode modules having integral waste containing cavities, with two point calibration being contemplated, along with the possibility of using external calibration fluid sources. This general state of the art may be summarized as follows:

| Prior Art Item | Disclosure |
|---|---|
| 1. Baker et al 4,654,127 | Disposable electrode (FIG. 8) module with integral waste cavity 20 and external, multiple point, calibration fluid source 40 (col. 11, lines 17–26) and external sample source 42. |
| 2. Diamond et al 4,272,245 | Disposable electrode module (FIG. 7) has an integral waste reservoir 98 with a vent 100. This disclosure contemplates the supplying of calibration fluid from an external source (col. 6, line 5). Possibility of two-point calibration noted at col. 6, line 38. The divisional Diamond et al patent 4,342,964 contains the same disclosure. |

—continued

| Prior Art Item | Disclosure |
|---|---|
| 3. Leiner et al 5,080,865 | Waste reservoir integral with electrode module, with vacuum to pull sample and two-point calibration fluids (gas) through system (see col. 9 at lines 6–17). |
| 4. Burleigh et al 4,734,184 | Disposable test module including waste reservoir and two-point calibration fluid sources. However, the waste reservoir and calibration fluid sources are all external of the electrode containing module (somewhat similar disclosures may be found in Enzer et al 4,786,394, Enzer et al 4,871,439, and Fong 5,328,848 (optical as opposed to electrode sensors)). |
| 5. Lauks et al 5,096,669 Morris et al 5,325,853 | Waste chamber integral with electrode module - but with calibration fluid also being integral. |
| 6. Sullivan 4,266,941 | External, pressurized aluminum cylinder for supplying calibration fluid to blood testing system. |

Additional state of the art disclosures include:

| U.S. Pat. No. | Patentee | Assignee |
|---|---|---|
| 4,301,412 | Hill et al | United States Surgical Corporation |
| 4,301,414 | Hill et al | United States Surgical Corporation |
| 4,336,121 | Enzer et al | Transidyne |
| 4,342,964 | Diamond et al | Transidyne |
| 4,397,725 | Enzer et al | Transidyne |
| 4,436,610 | Enzer et al | Transidyne |
| 4,535,786 | Kater | |
| 4,863,016 | Fong et al | Abbott Laboratories |
| 5,089,421 | Dieffenbach | |

These prior art teachings notwithstanding, the state of the art fails to suggest the characterizing combination of the present invention, as noted at the outset of this disclosure, with its attendant enhancement of POC, including POL, care and analysis.

SUMMARY OF INVENTION

Embodied in the novel combination concept noted above are separately significant inventive concepts which may be characterized as follows:

Disposable apparatus is provided for conducting patient testing and permitting multiple, two-point calibrated, test sequences, this apparatus comprising a disposable, sensing module having a sample receiving and analyzing station including a sample condition sensing electrode array operable to sequentially process a plurality of test sequences. A calibration fluid connecting station, integral with said sensing module, is provided for detachable connection to a first calibration fluid source and a second calibration fluid source. An analyte connecting station, integral with said sensing module, is provided for detachable connection to an analyte source. A flow passage network is operable to sequentially transmit to the electrode array a test sequence set including an amount of a first calibration fluid from the first calibration fluid source, an analyte from the analyte source; and an amount of the second calibration fluid from the second calibration fluid source. A sample and calibration fluid receiving chamber is provided which is integral with the sensing module, this chamber being wholly internal of the sensing module, operable to receive and contain a plurality of the test sequence sets, and in continuous communication with the analyzing station. The sensing module and integral sample and calibration fluid receiving chamber are separable from the first and second calibration fluid sources and disposable separately therefrom.

In addition, and of independent significance is a method of this invention for conducting patient testing and permitting multiple, two-point calibrated, test sequences, with disposable sensing modules. This method comprises providing a disposable, sensing module at a patient site having a sample receiving and analyzing station including a sample condition sensing electrode array operable to sequentially process a plurality of test sequences. A calibration fluid connecting station is provided which is integral with the sensing module. This method entails detachably connecting the calibration fluid connecting station to a first calibration fluid source and a second calibration fluid source. An analyte connection station is provided which is integral with the sensing module. This analyte connecting station is detachably connected to an analyte source. A flow passage network is operated to sequentially transmit to the electrode array a test sequence set including an amount of a first calibration fluid from the first calibration fluid source, an analyte from the analyte source, and an amount of a second calibration fluid from the second calibration fluid source. This sample and calibration fluid chamber is maintained integral with the sensing module, with this chamber being wholly internal of the sensing module, operable to receive and contain a plurality of said test sequence sets, and in continuous communication with the analyzing station. The sensing module and integral sample and calibration fluid receiving chamber are separated from the first and second calibration fluid sources and disposed of as mutually integrated components.

In a system format, the invention contemplates an apparatus for conducting patient testing and permitting multiple, two-point calibrated, test sequences, with this apparatus comprising a disposable, sensing module having a sample receiving and analyzing station, the latter including a sample condition sensing electrode array operable to sequentially process a plurality of test sequences. A first calibrating fluid source external of the sensing module is provided along with a second calibration fluid source external of the sensing module. A calibration fluid connecting station is provided which is integral with the sensing module, for detachable connection to the first calibration fluid source and the second calibration fluid source. An analyte source is provided which is external of the sensing module. An analyte connection station is integral with the sensing module, for detachable connection to the analyte source. A flow passage network is operable to sequentially transmit to the electrode array a test sequence set including an amount of a first calibration fluid from the first calibration fluid source, an analyte from the analyte source, and an amount of a second calibration fluid from the second calibration fluid source. A sample and calibration fluid receiving chamber integral with the sensing module is included, this chamber being wholly internal of the sensing module, operable to receive and contain a plurality of the aforesaid test sequence sets, and in continuous communication with the analyzing station. The sensing module and integral sample and calibration fluid receiving chamber are separable from the first and second calibration fluid sources and disposable separately therefrom.

Having described the general background of this technology and summarized basic aspects of the present invention, it is now appropriate to make reference to presently preferred embodiments illustrated by way of example in the appended drawings.

DRAWINGS

FIG. 1 schematically depicts a disposable, sensor module of the present invention;

FIG. 2 schematically illustrates a blood collection tube or adapter which may be employed with the FIG. 1 module;

FIG. 3 schematically depicts the FIG. 1 module interconnected with a representative blood collecting tube;

FIG. 4 schematically depicts the FIG. 1 module interconnected with a capillary tube interface;

FIG. 5 schematically depicts the FIG. 1 module interconnected with a direct vacutainer interface;

FIG. 6 schematically depicts the FIG. 1 module interconnected with a direct "A" line interface;

FIG. 7 schematically depicts the FIG. 1 module interconnected with a "A" line interface, using a syringe;

FIGS. 8a, 8b, and 8c schematically depict certain electrode configurations of the FIG. 1 module; and FIG. 9 schematically depicts a representative, possible arrangement for interfacing the FIG. 1 module with a source of first and second calibration fluid sources in the context of a control unit interfaced with a data input/output system.

DETAILED DESCRIPTION OF PRESENTLY PREFERRED EMBODIMENTS

Figure 1:
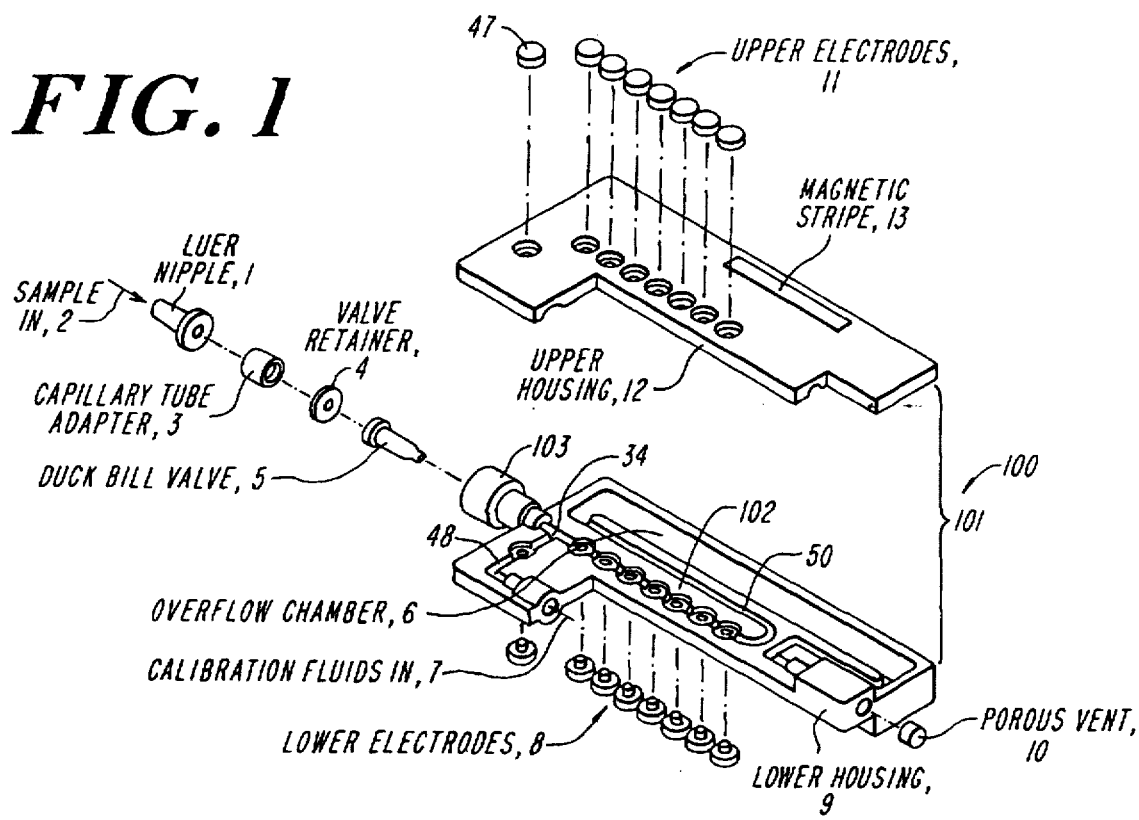

In the accompanying drawings, elements of the module and attached components are identified as follows:

| ELEMENT | FIG. | REFERENCE NUMERAL |
|---|---|---|
| Luer Nipple | 1 | 1 |
| Sample In | 1 | 2 |
| Capillary Tube Adapter | 1 | 3 |
| Valve Retainer | 1 | 4 |
| Duck Bill Valve | 1 | 5 |
| Overflow Chamber | 1 | 6 |
| Calibration Fluids Inlet | 1 | 7 |
| Lower Electrodes | 1 | 8 |
| Lower Housing | 1 | 9 |
| Porous Vent For Applying Negative Pressure | 1 | 10 |
| Upper Electrodes | 1 | 11 |
| Upper Housing | 1 | 12 |
| Magnetic Stripe For Counting Off Tests And Encoding Information | 1 | 13 |
| Hydrophobic Vent (4 plcs) | 2 | 14 |
| Rubber Plug | 2 | 15 |
| Housing | 2 | 16 |
| Duck Bill Valve | 2 | 17 |
| Valve Retainer | 2 | 18 |
| Luer Taper Both Ends | 2 | 19 |
| Cassette Housing | 3 | 20 (9 & 11 joined) |
| Blood Collection Tube | 3 | 21 |
| Rubber Plug Displaced By Cassette Luer | 3 | 15 |
| Cassette Housing | 4 | 20 |
| Luer Taper | 4 | 2 |
| Rubber Adapter Sleeve | 4 | 3 |
| Capillary Tube | 4 | 22 |
| Custom Adapter | 5 | 23 |
| Cassette Housing | 5 | 20 |
| Protective Sheath | 5 | 24 |
| Vacutainer | 5 | 25 |
| Blood Collection Tube | 6 | 21 |
| Custom Adapter | 6 | 26 |
| "A" Line Stopcock | 6 | 27 |
| Blood Collector Tube | 7 | 2 |
| Syringe | 7 | 28 |
| O₂ Electrode | 8a | 29 |
| Cassette Housing | 8a | 20 |
| Carbon Precious Metal | 8a | 30 |
| Hydrophilic Polymer Layer | 8a | 31 |
| O₂ Membrane | 8a | 32 |
| Electrode Contact | 8a | 33 |
| Fluid Path | 8a, 1 | 34 |

-continued

| ELEMENT | FIG. | REFERENCE NUMERAL |
|---|---|---|
| Thick Film Counter Reference | 8a | 35 |
| Cassette Housing | 8a | 20 |
| Reference/Counter | 8a | 36 |
| Electrode Contact | 8a | 37 |
| Cathode AG/AG CI Counter Reference | 8b | 38 |
| Cassette Housing | 8b | 20 |
| Counter/Reference | 8b | 39 |
| Electrode Contact | 8b | 40 |
| Fluid Path | 8b, 1 | 34 |
| Gox + Mediator | 8b | 41 |
| Cassette Housing | 8b | 20 |
| Anode Enzyme Electrode | 8b | 42 |
| Electrode Contact | 8b | 43 |
| Membrane | 8c | 44 |
| Cassette Housing | 8c | 20 |
| Electrode Contact | 8c | 45 |
| Thick Film Inner Reference (possibly located in calibration fluid path 48 or sample path 34, possibly near overflow path 50) | 8c | 46 |
| Reference Electrode | 8c, 1 | 47 |
| Calibraton Fluid Entry Path | 1, 8c | 48 |
| Analyte Entry Path | 1 | 34 (adjacent unit 103) |
| Network Path To Overflow (waste) Chamber | 1 | 50 |
| Calibration Fluid Source | 9 | 51 |
| Analyzer Control Housing With CPU Functions | 9 | 52 |
| External Input/Output Links Between Control Housing And External Data Input And/Or Receiving Means | 9 | 53 |
| External Data Input And/Or Receiving Means | 9 | 54 |
| Path To First Calibration Fluid Source | 9 | 55 |
| First Calibration Fluid Source | 9 | 56 |
| Path To Second Calibration Fluid Source | 9 | 57 |
| Second Calibration Fluid Source | 9 | 58 |
| Disposable Cassette Apparatus | 1 | 100 |
| Sensing Module | 1 | 101 |
| Analyzing Station | 1 | 102 |
| Analyte Connecting Station | 1 | 103 |

Element Relationships

From the delineation of components as set forth above and the depiction of these components in the illustrated drawings, the overall structure and mode of operation of aspects of the invention will be appreciated.

As is shown in FIG. 1, with the electrodes 8, 11, 47, (which may be conventional, commercially available units,) assembled in the upper and lower housings 9 and 11 and these housing components sealed together to define a closed assembly 101, a disposable apparatus 100 is provided comprising a sensing module 101 having an analyzing station 102 defined by the electrode array. An internal network of passages 103, 34, 48, 50, 6 permits the sequential flow of a first calibration fluid 56, an analyte from source 21, and a second calibration fluid 58. A vacuum applied at vent 10 may facilitate the flow of analytes while a vacuum or pressure source may induce the desired flow of calibration fluids.

Figure 9:
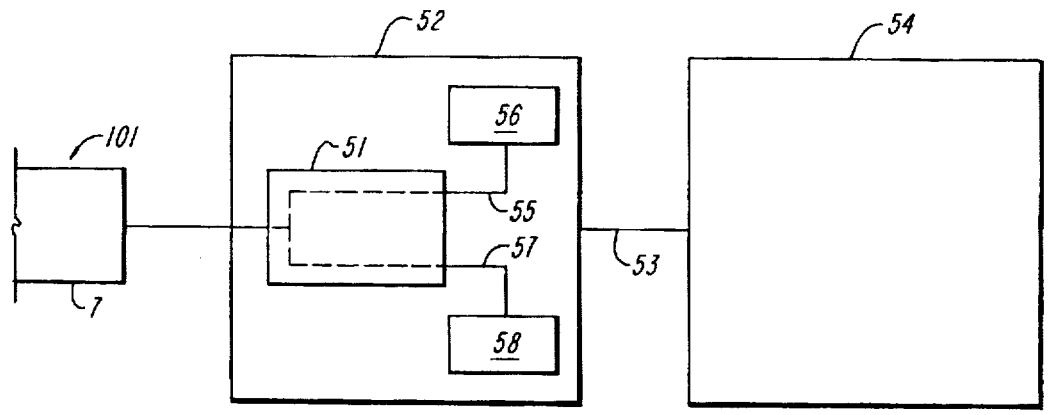

The module 101 (as schematically shown in FIG. 9) may be detachably connected to an analyzer control housing 52 having computer (CPU) functions, utilizing control mechanisms and connections known in the art.

In making this connection, as shown in FIG. 9, the calibration fluids inlet 7 of the module 101 may be connected with a calibration fluid source 51 providing flow paths leading to multiple calibration fluid sources. Thus, as is shown in FIG. 9 in a schematic sense, the calibration fluid source or connection 51 may provide an interface between the module 101 and a path 55 leading to a first source 56 of a first calibration fluid and, in parallel, or in some other conventional network arrangement, another flow path 57 leading to a second calibration fluid source 58.

The overall control unit 52 communicates by way of external input/output links or connections with an external data input and/or data receiving means 54. The latter may comprise keyboard input, bar code scanning input, printer output, output to modems, output to other units within a medical facility such as storage and/or analyzing units in a laboratory facility of a hospital or doctor's office, etc. The magnetic strip 13 on module 101 facilitates test counting and information encoding.

Figure 2:
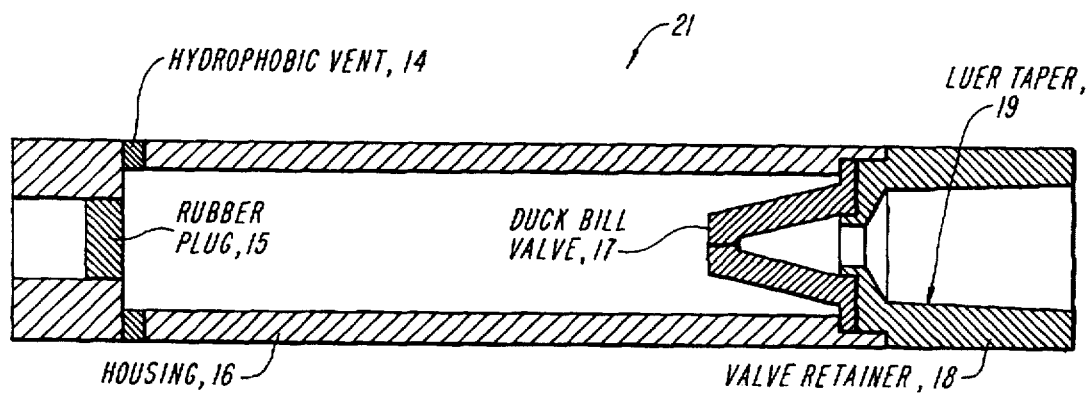
Figure 4:
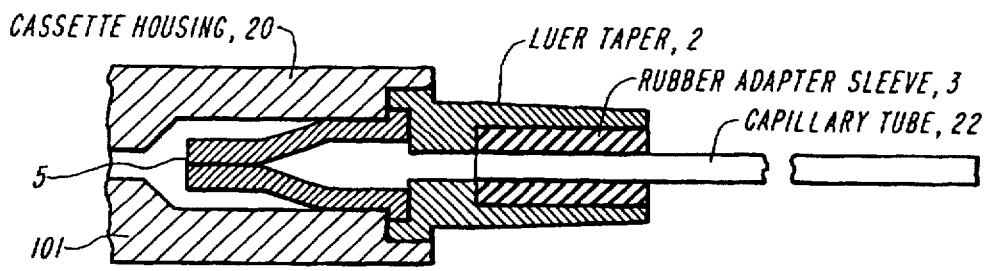
Figure 6:
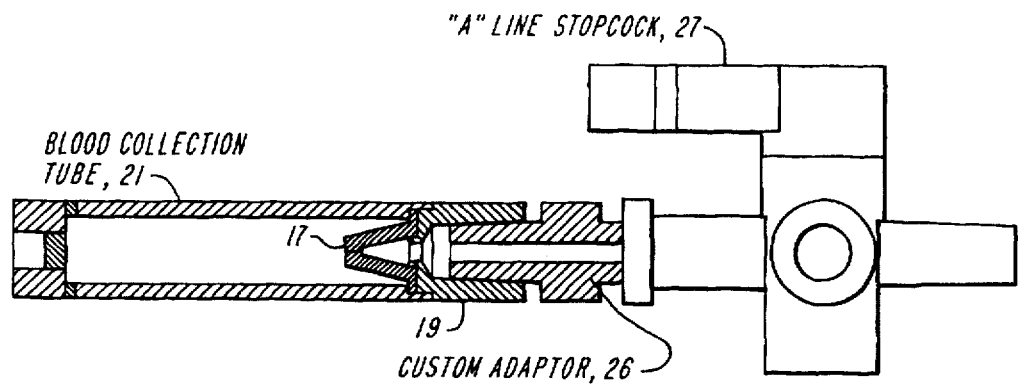
Figure 7:
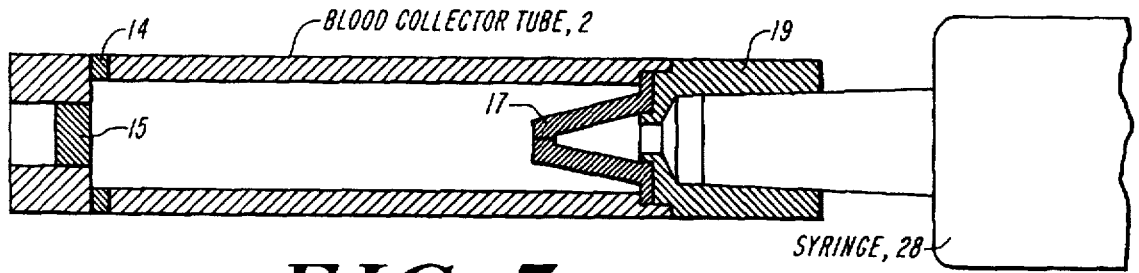

The module 101 is selectively associated with the desired analyte source, representative embodiments of which are illustrated in FIGS. 3, 4, 5, 6 and 7. As is shown in FIG. 2, this interfacing of the module 101 with a suitable or desired analyte source is facilitated by an adapter module or blood collection tube 21, preferably providing Luer connections between the module 101, an analyte source, and the module 101 itself.

Figure 8A:
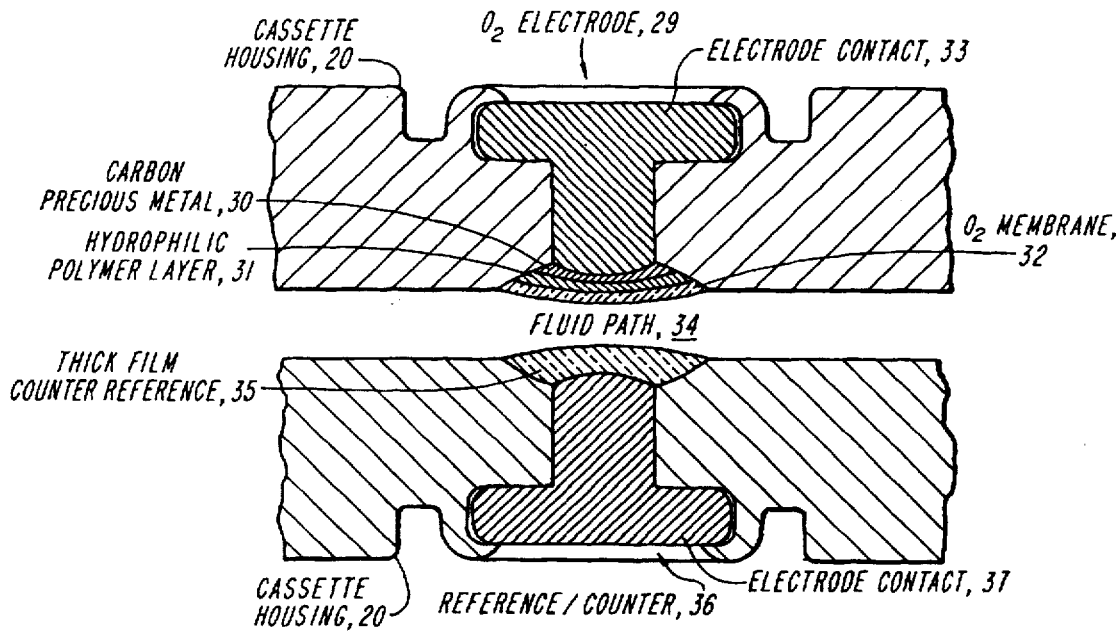
Figure 8B:
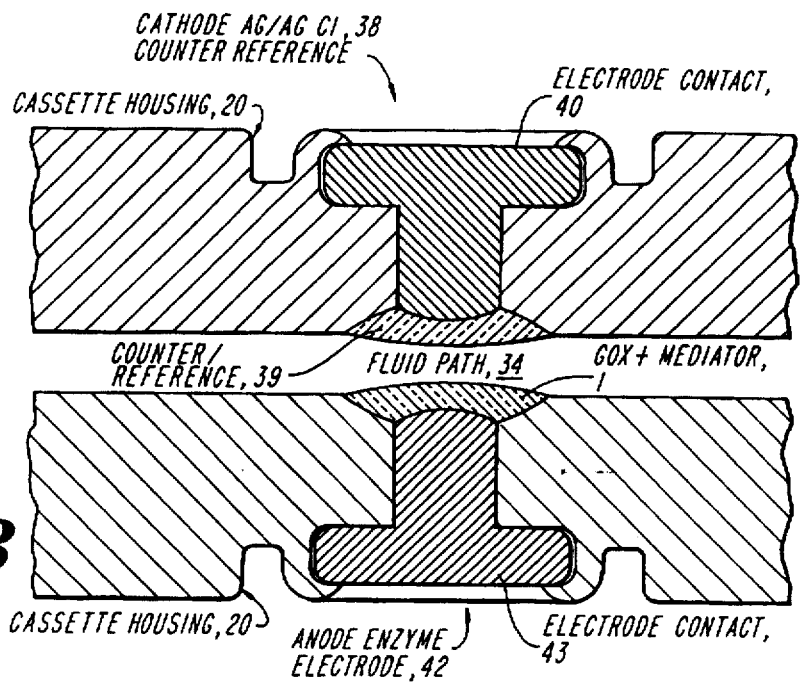
Figure 8C:
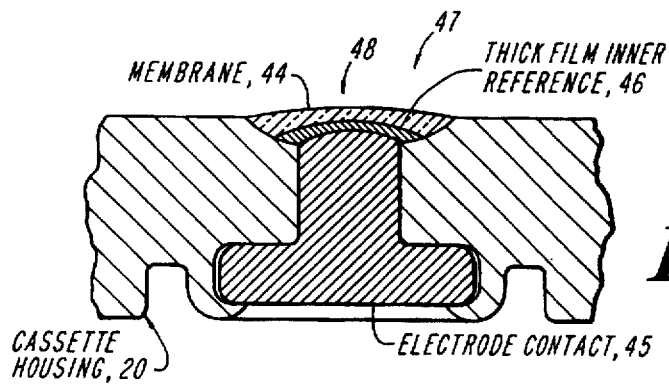

The exemplary prior art noted at the outset of this disclosure depicts a variety of button-type electrode configurations which may be employed in a connection with a variety of analyte analyzing techniques. FIGS. 8a and 8b illustrate, by way of example, representative configurations for oxygen and enzyme/glucose electrodes, with FIG. 8c providing a schematic illustration of a reference electrode 48.

From the foregoing identification of apparatus elements and the depiction of the relationships of these elements in the appended drawings, it is believed that those familiar with this presentation and skilled in this art will immediately recognize the manner in which the elements of the invention are interrelated and function.

In this connection, it will be recognized the electrode elements, mechanisms for interconnecting assemblies, component materials, etc. all involve parameters and techniques within the skill of the art, as evidenced by the state of the art reviewed at the outset of this disclosure.

While particular configurations, as set forth and illustrated in the drawings and referred to in the foregoing compilation, are believed to be particularly efficacious from the standpoint of providing a uniquely effective and enhanced point-of-care module, accomplishing the basic objectives of the invention set forth at the outset of this disclosure, it will be recognized that individual elements as featured in the prior art, and exemplified by the compilation above, may be selectively employed.

All this notwithstanding, this invention resides in combination concepts which will now be summarized with reference to the specific elements identified above and correspondingly labeled in the appended drawings.

Summary of Combination Concepts

Embodied in the novel combination concept noted above are separately significant inventive concepts which may be characterized as follows:

Disposable apparatus 100 is provided for conducting patient testing and permitting multiple, two-point calibrated, test sequences, this apparatus comprising a disposable, sensing module 101 having a sample receiving and analyzing station 102 including a sample condition sensing electrode array 8, 11, 47 operable to sequentially process a plurality of test sequences. A calibration fluid connecting station 7, integral with said sensing module 101, is provided for detachable connection to a first calibration fluid source 56 and a second calibration fluid source 58. An analyte connecting station 103, integral with said sensing module, is provided for detachable connection to an analyte source 21. A flow passage network 103, 7, 34, 48 is operable to sequentially transmit to the electrode array a test sequence set including an amount of a first calibration fluid from the first calibration fluid source 56, an analyte from the analyte source 21; and an amount of the second calibration fluid from the second calibration fluid source 58. In this connection, it is to be appreciated that for certain runs, in a sampling sequence, it may be possible to dispense with the use of the first calibrating fluid. However, periodically, calibration runs with both calibration fluids would be employed. A sample and calibration fluid receiving chamber 6 is provided which is integral with the sensing module, this chamber 6 being wholly internal of the sensing module 101, operable to receive and contain a plurality of the test sequence sets, and in continuous communication with the analyzing station 102. The sensing module 101 and integral sample and calibration fluid receiving chamber 6 are separable from the first and second calibration fluid sources 56 and 58 and disposable separately therefrom.

In addition, and of independent significance is a method of this invention for conducting patient testing and permitting multiple, two-point calibrated, test sequences, with disposable sensing modules. This method comprises providing a disposable, sensing module 101 at a patient site (POC or POL) having a sample receiving and analyzing station 102 including a sample condition sensing electrode array 8, 11, 47 operable to sequentially process a plurality of test sequences. A calibration fluid connecting station 7 is provided which is integral with the sensing module 101. This method entails detachably connecting the calibration fluid connecting station 7 to a first calibration fluid source 56 and a second calibration fluid source 58. An analyte connection station is provided which is integral with the sensing module. This analyte connecting station 103 is detachably connected to an analyte source such as 21, for example. A flow passage network 103, 7, 34, 48 is operated to sequentially transmit to the electrode array a test sequence set including an amount of a first calibration fluid from the first calibration fluid source 56, an analyte from the analyte source 21, and an amount of a second calibration fluid from the second calibration fluid source 58. This sample and calibration fluid receiving chamber is maintained integral with the sensing module 101, with this chamber 6 being wholly internal of the sensing module 101, operable to receive and contain a plurality of said test sequence sets, and in continuous communication with the analyzing station 102. The sensing module 101 and integral sample and calibration fluid receiving chamber 6 are separated from the first and second calibration fluid sources 56 and 58 and disposed of as mutually integrated components.

In a system format, the invention contemplates an apparatus 100 for conducting patient testing and permitting multiple, two-point calibrated, test sequences, with this apparatus comprising a disposable, sensing module 101 having a sample receiving and analyzing station 102, the latter including a sample condition sensing electrode array 8, 11, 47 operable to sequentially process a plurality of test sequences. A first calibrating fluid source 56 external of the sensing module 101 is provided along with a second calibration fluid source 58 external of the sensing module 101. A calibration fluid connecting station 7 is provided which is integral with the sensing module 101, for detachable connection to the first calibration fluid source 56 and the second calibration fluid source 58. An analyte source 21 is provided which is external of the sensing module 101. An analyte connection station 103 is integral with the sensing module 101, for detachable connection to the analyte source 21. A flow passage network 103, 7, 34, 48 is operable to sequentially transmit to the electrode array 8, 11, 47 a test sequence set including an amount of a first calibration fluid from the first calibration fluid source 56, an analyte from the analyte source 21 and an amount of a second calibration fluid from the second calibration fluid source 58. A sample and calibration fluid receiving chamber 6 integral with the sensing module 101 is included, this chamber 6 being wholly internal of the sensing module 101, operable to receive and contain a plurality of the aforesaid test sequence sets, and in continuous communication with the analyzing station 102. The sensing module 101 and integral sample and calibration fluid receiving chamber 6 are separable from the first and second calibration fluid sources 56 and 58 and disposable separately therefrom.

In each of the foregoing aspects there may also be provided an analyte source or collection unit 21, a first detachable connection 1 for detachably connecting the unit 21 to the analyte connecting station 103, and a second detachable connection 19 for detachably connecting the unit 21 to an analyte supply such as 22, etc.

Further refinements may include porous vent means 10 for creating a pressure differential across said flow passage network 6, 34, 48, 7, 103 operable to induce fluid flow there through, leading to said receiving chamber 6. Vent means would be connected to a conventional vacuum source for this purpose.

As will be appreciated, the foregoing discussion is directed to those skilled in this art.

Accordingly, obfuscation of the present invention by unnecessary detailing of electrode structures, types, component mounting details, etc. has been avoided since such features are well known. Moreover, such arrangements in this respect as have been noted are disclosed only by way of general example.

SUMMARY OF ADVANTAGES AND OVERALL SCOPE OF INVENTION

A particularly advantageous aspect of the invention relies in the provision of a multi-condition sensing, disposable sensor module which is operable to cooperate with multiple fluid sources to provide multi-point calibration, with the sources being detachable from the sensor module and with an integral waste reservoir being provided which is operable to receive complete multiple test sequences including calibration fluids and analyte.

This combination provides a uniquely versatile, convenient, and compact assembly, particularly adapted to point-of-care utilization.

Those skilled in this art and familiar with the present disclosure may well recognize additions, deletions, substitutions, and other purview of the invention which would fall within the purview of the invention which is defined in the appended claims.

I claim:

1. Disposable apparatus for conducting patient testing and permitting multiple, two-point calibrated, test sequences, said apparatus comprising:

a disposable, sensing module having
a sample receiving and analyzing station including
a sample condition sensing electrode array operable to sequentially process a plurality of test sequences;
a calibration fluid connecting station, integral with said sensing module, for detachable connection to a first calibration fluid source; and
a second calibration fluid source;
an analyte connecting station, integral with said sensing module, for detachable connection to an analyte source;
a flow passage network operable to sequentially transmit to said electrode array a test sequence set including
an amount of a first calibration fluid from said first calibration fluid source;
an analyte from said analyte source; and
an amount of a second calibration fluid from said second calibration fluid source;
a sample and calibration fluid receiving chamber integral with said sensing module, said chamber being
wholly internal of said sensing module,
operable to receive and contain a plurality of said test sequence sets, and
in continuous communication with said analyzing station;
said sensing module and integral sample and calibration fluid receiving chamber being separable from said first and second calibration fluid sources and disposable separately therefrom;
a first calibration fluid source detachably connected with said calibration fluid connecting station of said sensing module, with
said first calibration fluid source being separable from said sensing module
said sensing module being disposable separately from said first calibration fluid source and
said first calibration fluid source being disposed externally of said sensing module;
a second calibration fluid source detachably connected with said calibration fluid connecting station of said sensing module, with
said second calibration fluid source being separate from said first calibration fluid source,
said second calibration fluid source being separable from said sensing module,
said sensing module being disposable separately from said second calibration fluid source, and
said second calibration fluid source being disposed externally of said sensing module;
said calibration fluid connecting station being disposed separately from and operably independent of, said analyte connecting station, with
said calibration fluid connecting station being operable to receive calibration fluid from each of said first and second calibration fluid sources independent of said analyte connecting station; and
each of said first and second calibration fluid sources being disposed externally of, and separable from, said sensing module and integral sample and calibration fluid receiving chamber.

2. An apparatus as described in claim 1 further comprising:
an analyte collection unit;
a first detachable connection for detachably connecting said unit to said analyte connecting station; and
a second detachable connection for detachably connecting said unit to an analyte source.

3. An apparatus as described in claim 2 including:
means for creating a pressure differential across said flow passage network operable to induce fluid flow there through, leading to said receiving chamber.

4. A method for conducting patient testing and permitting multiple, two-point calibrated, test sequences, with disposable sensing modules, said method comprising:

providing a disposable, sensing module at a patient site having
a sample receiving and analyzing station including
a sample condition sensing electrode array operable to sequentially process a plurality of test sequences;
providing a calibration fluid connecting station, integral with said sensing module, and detachable connecting said calibration fluid connecting station to
a first calibration fluid source; and
a second calibration fluid source;
providing an analyte connecting station, integral with said sensing module, and
detachably connecting said analyte connecting station to an analyte source;
operating a flow passage network to sequentially transmit to said electrode array a test sequence set including
an amount of a first calibration fluid from said first calibration fluid source;
an analyte from said analyte source; and
an amount of a second calibration fluid from said second calibration fluid source;
maintaining a sample and calibration fluid chamber integral with said sensing module, with said chamber being
wholly internal of said sensing module,
operable to receive and contain a plurality of said test sequence sets, and
in continuous communication with said analyzing station;
separating said sensing module and integral sample and calibration fluid receiving chamber from said first and second calibration fluid sources and disposing of said sensing module and chamber as mutually integrated components;
prior to said operating of said flow passage network, providing a first calibration fluid source detachably connected with said calibration fluid connecting station of said sensing module, with
said first calibration fluid source being separable from said sensing module,
said sensing module being disposable separately from said first calibration fluid source, and
said first calibration fluid source being disposed externally of said sensing module;
prior to said operating of said flow passage network, providing a second calibration fluid source detachably connected with said calibration fluid connecting station of said sensing module, with
said second calibration fluid source being separate from said first calibration fluid source,
said second calibration fluid source being separable from said sensing module,
said sensing module being disposable separately from said second calibration fluid source, and
said second calibration fluid source being disposed externally of said sensing module;
prior to said operating of said flow passage network, disposing said calibration fluid connecting station separately from, and operably independent of, said analyte connecting station, with
said calibration fluid connecting station being operable to receive calibration fluid from each of said first and second calibration fluid sources independent of said analyte connecting station; and
prior to said operating of said flow passage network, disposing each of said first and second calibration fluid sources externally of, and separable from, said sensing module and integral sample and calibration fluid receiving chamber.

5. A method as described in claim 4 further comprising:

providing an analyte collection unit;

providing a first detachable connection for detachably connecting said unit to said analyte connecting station; and providing a second detachable connection for detachably connecting said unit to an analyte source.

6. A method as described in claim 5 including:

creating a pressure differential across said flow passage network operable to induce fluid flow there through, leading to said receiving chamber.

7. Apparatus for conducting patient testing and permitting multiple, two-point calibrated, test sequences, said apparatus comprising:

a disposable, sensing module having
   a sample receiving and analyzing station including
      a sample condition sensing electrode array operable to sequentially process a plurality of test sequences;

a first calibrating fluid source external of said sensing module;

a second calibration fluid source external of said sensing module;

a calibration fluid connection station, integral with said sensing module, for detachable connection to
   said first calibration fluid source; and
   said second calibration fluid source;

an analyte source external of said sensing module;

an analyte connecting station, integral with said sensing module, for detachable connection to said analyte source;

a flow passage network operable to sequentially transmit to said electrode array a test sequence set including
   an amount of a first calibration fluid from said first calibration fluid source;
   an analyte from said analyte source;
   an amount of a second calibration fluid from said second calibration fluid source;

a sample and calibration fluid receiving chamber integral with said sensing module, said chamber being
   wholly internal of said sensing module,
   operable to receive and contain a plurality of said test sequence sets, and
   in continuous communication with said analyzing station;

said sensing module and integral sample and calibration fluid receiving chamber being separable from said first and second calibration fluid sources and disposable separately therefrom;

said first calibration fluid source being detachably connected with said calibration fluid connecting station of said sensing module with
   said first calibration fluid source being separable from said sensing module,
   said sensing module being disposable separately from said first calibration fluid source, and
   said first calibration fluid source being disposed externally of said sensing module;

said second calibration fluid source being detachably connected with said calibration fluid connecting station of said sensing module, with
   said second calibration fluid source being separate from said first calibration fluid source,
   said second calibration fluid source being separable from said sensing module,
   said sensing module being disposable separately from said second calibration fluid source, and
   said second calibration fluid source being disposed externally of said sensing module;

said calibration fluid connecting station being disposed separately from, and operably independent of, said analyte connecting station, with
   said calibration fluid connecting station being operable to receive calibration fluid from each of said first and second calibration fluid sources independent of said analyte connecting station; and each of said first and second calibration fluid sources being disposed externally of, and separable from, said sensing module and integral sample and calibration fluid receiving chamber.

8. An apparatus as described in claim 7 further comprising:

an analyte collection unit;

a first detachable connection for detachably connecting said unit to said analyte connecting station; and a second detachable connection for detachably connecting said unit to an analyte source.

9. An apparatus as described in claim 8 including:

means for creating a pressure differential across said flow passage network operable to induce fluid flow there through, leading to said receiving chamber.

* * * * *